US00PP29149P2

(12) United States Plant Patent
Verhoef

(10) Patent No.: US PP29,149 P2
(45) Date of Patent: Mar. 27, 2018

(54) ***WEIGELA* PLANT NAMED 'SLINGPINK'**

(50) Latin Name: ***Weigela* hybrid**
Varietal Denomination: Slingpink

(71) Applicant: Gijsbertus Verhoef, Hazerswoude (NL)

(72) Inventor: Gijsbertus Verhoef, Hazerswoude (NL)

( * ) Notice: Subject to any disclaimer, the term of this patent is extended or adjusted under 35 U.S.C. 154(b) by 0 days.

(21) Appl. No.: 15/530,580

(22) Filed: Feb. 1, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para

(57) ABSTRACT

A new cultivar of *Weigela* plant named 'Slingpink' that is characterized by green foliage, a dense compact plant habit, light pink flowers and repeat flowering from May to October.

1 Drawing Sheet

Botanical classification: *Weigela* hybrid.
Variety denomination: 'Slingpink'.

BACKGROUND OF THE INVENTION

The present invention relates to a new and distinct cultivar of *Weigela* plant botanically known as *Weigela* hybrid and hereinafter referred to by the cultivar name 'Slingpink'.

The new cultivar is the product of a breeding program conducted by the inventor in a cultivated area of Hazerswoude, The Netherlands. The objective of the breeding program was to develop new *Weigela* cultivars that are compact growing, repeat flowering and have attractive flower colors.

'Slingpink' originated from the crossing of the female or seed parent *Weigela* 'Slingco 1' (U.S. Plant Pat. No. 23,654) and the male or pollen parent, an unnamed proprietary *Weigela* cultivar in 2012. The cultivar 'Slingpink' was selected by the inventor in 2014 as a single plant within the progeny of the stated cross in a cultivated area of Hazerswoude, The Netherlands.

Asexual reproduction by softwood cuttings of the new cultivar 'Slingpink' was first performed in 2014 in Hazerswoude, The Netherlands. Since that time, under careful observation, the unique characteristics of the new *Weigela* cultivar have been uniform, stable and reproduced true to type in successive generations of asexual reproduction.

SUMMARY OF THE INVENTION

The following represent the distinguishing characteristics of the new *Weigela* cultivar 'Slingpink'. These traits in combination distinguish 'Slingpink' as a new and distinct cultivar apart from other existing varieties of *Weigela* known to the inventor. 'Slingpink' has not been tested under all possible conditions and phenotypic differences may be observed with variations in environmental, climatic, and cultural conditions, however, without any variance in genotype.

1. *Weigela* 'Slingpink' exhibits a dense compact plant habit.
2. *Weigela* 'Slingpink' exhibits light pink flowers.

3. *Weigela* 'Slingpink' exhibits repeat flowering from May to October.
4. *Weigela* 'Slingpink' exhibits green foliage.

The closest comparison plants are *Weigela* 'Plangen' (not patented) and *Weigela* 'Minuet' (not patented). The new cultivar 'Slingpink' is distinguishable from 'Plangen' in the following characteristics:

1. 'Slingpink' exhibits a more compact plant habit than 'Plangen'.
2. 'Slingpink' exhibits repeat flowering from May to October. In contrast, 'Plangen' flowers from May to mid-June.

The new cultivar 'Slingpink' is distinguishable from 'Minuet' in the following characteristics:

1. 'Slingpink' exhibits a more compact plant habit than 'Minuet'.
2. 'Slingpink' exhibits repeat flowering from May to October. In contrast, 'Minuet' flowers from May to mid-June.
3. 'Slingpink' exhibits light pink flowers. In contrast, the flowers of 'Minuet' are purple-pink in color.

The new cultivar 'Slingpink' is distinguishable from the female parent plant 'Slingco 1' in having light pink flowers. In contrast, the flowers of 'Slingco 1' are red.

The new cultivar 'Slingpink' is distinguishable from the male parent plant in having a more compact habit and repeat flowering from May to October. In contrast, the male parent plant flowers from May to mid-June.

BRIEF DESCRIPTION OF THE DRAWING

The accompanying photograph illustrates the distinguishing traits of *Weigela* 'Slingpink'. The plant in the photograph shows an overall view of a 21 month old outdoor grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Weigela* cultivar named 'Slingpink'. Data was collected in Hazerswoude, The Netherlands from 21 month old plants grown outdoors in 28 cm. (10 liter) containers. The time of year was May and the temperatures ranged from 12-22° Centigrade during the day and 6-14° Centigrade during the night. The light level was natural outdoor light and there were no photoperiodic treatments or growth retardants used. Color determinations are in accordance with The Royal Horticultural Society Colour Chart, $6^{th}$ edition 2015, except where general color terms of ordinary dictionary significance are used. The growing requirements are similar to the species.

Botanical classification: *Weigela* hybrid 'Slingpink'.

Parentage: 'Slingpink' resulted from the crossing of the female or seed parent *Weigela* 'Slingco 1' and the male or pollen parent, an unnamed proprietary *Weigela* cultivar.

Annual or perennial: Perennial.

Plant type: Shrub.

Suitable container size: 13 cm. and larger.

Plant shape: Flattened globe shaped.

Growth habit: Woody plant with main branches and lateral branches.

Height to top of foliar plane: Average 23.6 cm.

Height to top of floral plane: Average 22.9 cm.

Width: Average 38.2 cm. in diameter.

Vigor: Moderate.

Growth rate: Moderate.

Low temperature tolerance: −25 degrees Centigrade (USDA Zone 5).

High temperature tolerance: 35 degrees Centigrade.

Propagation: Softwood cuttings.

Time to initiate roots: 21 to 28 days are required to initiate roots at 18 degrees Centigrade in the summer.

Time to produce a rooted plant: 60 days are required to produce a rooted plant at 16-22 degrees Centigrade in the summer.

Crop time: Approximately 13 months are required to achieve a finished plant.

Root system: Main roots moderately thick, other roots moderately fine.

Stem:

- *Branching habit.*—Free branching.
- *Basal branching.*—Yes.
- *Average number of main branches per plant.*—6.
- *Average number of lateral branches per plant.*—35.
- *Pinching.*—Not required, pinching will improve branching.
- *Lateral branch diameter.*—Average 4 mm. in diameter.
- *Lateral branch length.*—Average 9.7 cm. in length.
- *Internode length.*—Approximately 2.6 cm. between nodes.
- *Stem appearance.*—Slightly quadrangular in shape.
- *Stem luster.*—Moderately glossy.
- *Stem aspect.*—Average angle 37.5 degrees from vertical.
- *Stem strength.*—Moderately strong.
- *Stem color immature.*—144A to 144B.
- *Stem color mature.*—144A to 144B.
- *Internode color.*—144A to 144B.
- *Bark color.*—199B to 199C.
- *Pubescence.*—Young stems covered with soft adpressed hairs, average 0.3 mm. in length.

Foliage:

- *Leaf arrangement.*—Opposite.
- *Compound or single.*—Single.
- *Quantity of leaves per lateral branch.*—Average 8.
- *Leaf shape.*—Narrow obovate to elliptic.
- *Leaf tip.*—Apiculate.
- *Leaf base.*—Cuneate.
- *Leaf margin.*—Serrate.
- *Leaf dimensions.*—Length 7.5 cm; width 3.0 cm.
- *Leaf lobed.*—Not lobed.
- *Leaf texture* (*both sides*).—Smooth.
- *Leaf luster.*—Upper side glossy, under side slightly glossy.
- *Leaf rugosity.*—Upper side slightly rugose, under side not rugose.
- *Pubescence* (*both sides*).—Moderately covered with soft hairs, 0.5 mm. in length, color 157D, main vein on under side densely covered with soft hairs.
- *Vein pattern.*—Pinnate.
- *Leaf color young, upper surface.*—Between 143B and 144A, margins 174A.
- *Leaf color young, lower surface.*—146B to 146C.
- *Leaf color mature, upper surface.*—NN137A.
- *Leaf color mature, lower surface.*—147B.
- *Vein color, upper side.*—144B.
- *Vein color, under side.*—145B.
- *Leaf attachment.*—Petiolate.

Petiole:

- *Petiole dimensions.*—3.0 mm. in length and 1.75 mm. in diameter.
- *Petiole texture.*—Smooth.
- *Petiole luster.*—Slightly glossy.
- *Petiole pubescence.*—Soft hairs, 0.5 mm. in length, color 157D.
- *Petiole strength.*—Moderately strong.
- *Petiole color.*—Upper side N144A, under side 144B.

Inflorescence:

- *Inflorescence type.*—Compound cyme.
- *Inflorescence height.*—6.1 cm. including peduncle.
- *Inflorescence diameter.*—6.6 cm.
- *Quantity of flowers per inflorescence.*—Average 9.
- *Quantity of flowers per plant.*—Average 150.
- *Quantity of flower buds per plant.*—Average 50.
- *Quantity of flowers and flower buds per plant.*—Average 200.
- *Natural flowering season.*—May to October in the Netherlands.
- *Time to flower from planting.*—Approximately 8 months.

Flower buds:

- *Bud length.*—Average 3.2 cm.
- *Bud diameter.*—Average 9 mm. in diameter.
- *Bud shape.*—Oblanceolate.
- *Bud texture.*—Smooth.
- *Bud luster.*—Matte.
- *Bud pubescence.*—Moderately covered with soft hairs, 0.5 mm. in length.
- *Bud color.*—50B to 50C, tip 50A, fading to 155A at base.

Flower:

- *Flower type.*—Single, campanulate.
- *Flower aspect.*—Outward to upright.
- *Flowering habit.*—Freely.
- *Fragrance.*—None.
- *Flower shape.*—Campanulate.
- *Flower dimensions.*—Average 1.6 cm. in diameter and 3.8 cm. in height.
- *Flower throat diameter.*—Average 7.0 mm.
- *Flower throat texture.*—Smooth.

*Flower tube dimensions*.—Average 2.8 cm. in length and 4.0 mm. in diameter.
*Flower tube texture*.—Smooth.
*Flower longevity*.—Approximately 12 days.
*Persistent or self-cleaning*.—Self-cleaning.

Petals:
*Petal arrangement*.—Rotate, fused into a campanulate corolla.
*Number of petals*.—Five in number.
*Number of petal whorls*.—One.
*Petals fused*.—Yes, lower 75% fused.
*Petal dimensions*.—Average 3.8 cm. in length and free part 8.0 mm. in width.
*Petal shape*.—Spathulate.
*Petal margin*.—Entire.
*Petal apex*.—Obtuse, revolute.
*Petal base*.—Fused.
*Petal luster*.—Matte both sides.
*Petal texture*.—Smooth both sides.
*Petal rugosity*.—Not rugose both sides.
*Petal color when opening* (*upper side*).—11B, margins 58C.
*Petal color when opening* (*under side*).—50C, tip 50A to 50B.
*Petal color fully opened* (*upper side*).—1C and 1D to 2D, 46A. fading toward margins 50C to 50D.
*Petal color fully opened* (*under side*).—50C, tip 50B.
*Petal veins*.—None visible.
*Petal color fading to*.—Not fading.
*Flower throat color* (*upper side*).—1C and 1D to 2D, blotch on one petal 13A fading to 167A.
*Flower throat color* (*under side*).—1D.
*Flower throat veins*.—None visible.
*Flower tube color*.—1D both sides.

Calyx:
*Calyx shape*.—Rotate.
*Calyx dimensions*.—Average 1.0 cm. in length and 9.0 mm. in diameter.

Sepals:
*Sepal arrangement*.—Rotate.
*Number of sepals*.—Average 5.
*Number of sepal whorls*.—Average 1.
*Sepal dimensions*.—Average 1.0 cm. in length and 0.8 mm. in width.
*Sepals fused*.—Not fused.
*Sepal shape*.—Linear.
*Sepal apex*.—Narrow acute.
*Sepal base*.—Cuneate.
*Sepal margin*.—Entire.
*Sepal texture* (*both sides*).—Smooth; sparsely covered with soft hairs 0.5 mm. in length.
*Sepal luster*.—Matte both sides.
*Sepal color, young* (*upper side*).—143A, fading toward base 144C.
*Sepal color, young* (*under side*).—152C to 152D, fading lighter toward base 144C.
*Sepal color, mature* (*upper side*).—143A, fading toward base 144C.
*Sepal color, mature* (*under side*).—152C to 152D, fading lighter toward base 144C.
*Sepal spurs*.—Absent.

Peduncle:
*Peduncle dimensions*.—Average 1.0 cm. in length and 1.5 mm. in diameter.
*Peduncle angle*.—Average 0 degrees from lateral branch axis.
*Peduncle strength*.—Moderately strong.
*Peduncle texture*.—Smooth, sparsely covered with soft hairs 0.5 mm. in length.
*Peduncle luster*.—Slightly glossy.
*Peduncle color*.—145A.

Pedicels:
*Pedicel dimensions*.—Average 1.5 cm. in length and 1.0 mm. in diameter.
*Pedicel angle*.—20 degrees from peduncle axis.
*Pedicel strength*.—Moderately strong.
*Pedicel texture*.—Smooth, sparsely covered with soft hairs 0.5 mm. in length.
*Pedicel luster*.—Slightly glossy.
*Pedicel color*.—144A to 144B.

Reproductive organs:
*Stamen number*.—Average 5.
*Filament length*.—10 mm, filaments implanted in petals.
*Filament color*.—150D.
*Anther shape*.—Narrow oblong.
*Anther dimensions*.—5.0 mm. in length and 0.6 mm. in width.
*Anther color*.—150D.
*Amount of pollen*.—Moderate.
*Pollen color*.—161D.
*Number of pistils*.—Average 1.
*Pistil length*.—3.1 cm.
*Stigma shape*.—Club shaped.
*Stigma dimensions*.—1.5 mm. in length and 2.5 mm. in diameter.
*Stigma color*.—150B to 150C.
*Style length*.—2.95 cm.
*Style color*.—145B, tinged 179B.
*Ovary color*.—144A to 144B.

Fruit and seed production: Fruit and seed development has not been observed to date.

Disease and pest resistance: Disease and pest resistance has not been observed to date.

The invention claimed is:

1. A new and distinct variety of *Weigela* plant named 'Slingpink' as described and illustrated.

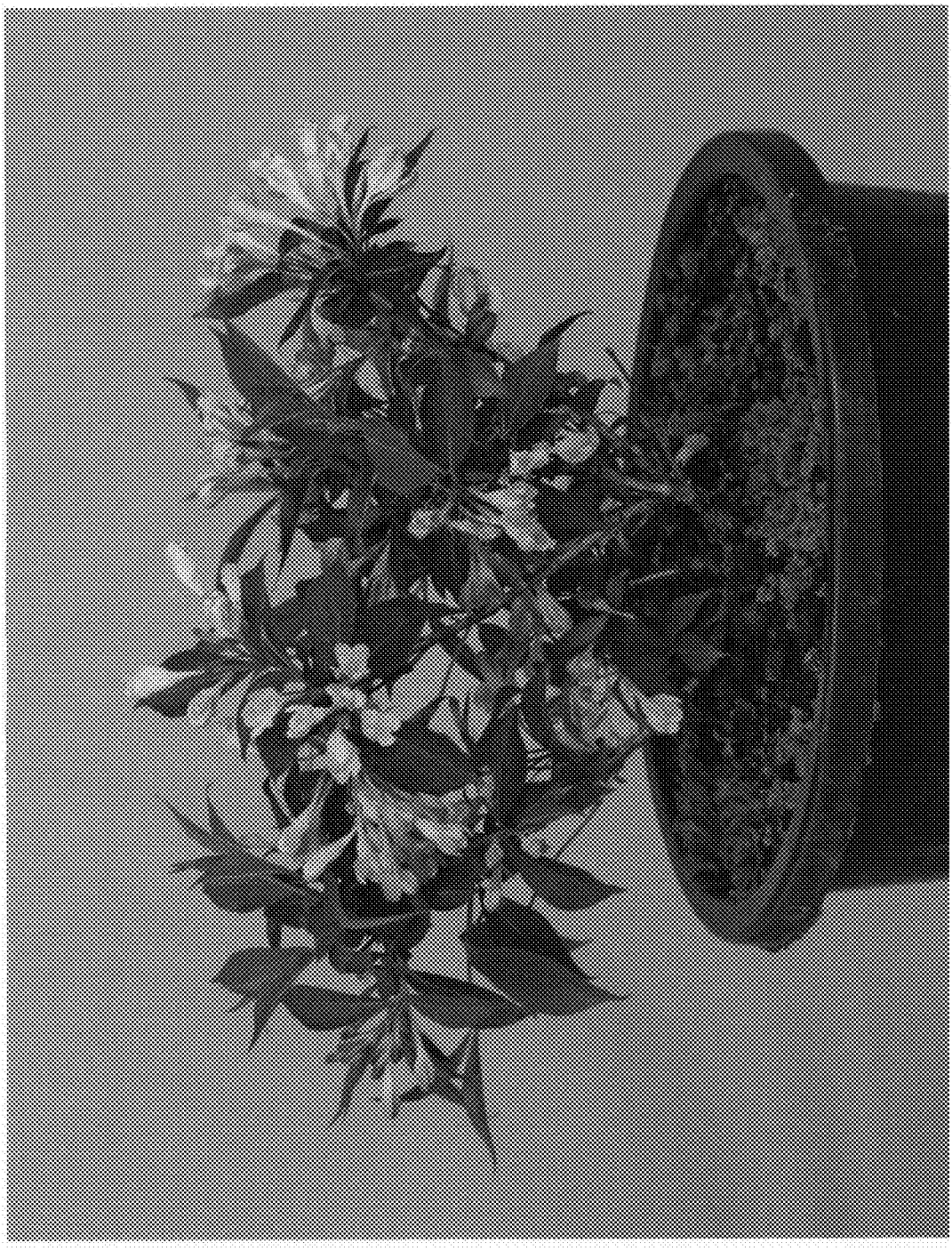

* * * * *